United States Patent [19]

Bagwell et al.

[11] Patent Number: 5,396,884
[45] Date of Patent: Mar. 14, 1995

[54] HIGH FLOW RATE HUMIDIFIER WITH BAFFLE PLATES

[75] Inventors: James T. Bagwell, Anaheim; Blair E. Howe, Rancho Santa Margarita, both of Calif.

[73] Assignee: Cimco, Inc., Costa Mesa, Calif.

[21] Appl. No.: 52,653

[22] Filed: Apr. 26, 1993

Related U.S. Application Data

[63] Continuation of Ser. No. 794,733, Nov. 15, 1991, abandoned.

[51] Int. Cl.$^6$ .................. A61M 11/00; B05B 1/26
[52] U.S. Cl. ................. 128/200.21; 128/200.18; 261/DIG. 65; 239/338
[58] Field of Search ............. 128/200.14, 200.18, 128/200.21, 203.12, 203.15–203.17, 203.26, 203.27, 204.27; 55/257.6; 261/DIG. 65; 239/338

[56] References Cited

U.S. PATENT DOCUMENTS

| | | | |
|---|---|---|---|
| 1,040,801 | 10/1912 | Snyder | 128/203.29 |
| 2,381,558 | 8/1945 | Robinson | 299/88.5 |
| 2,600,503 | 6/1952 | Gauchard | 128/200.18 |
| 2,622,593 | 12/1952 | Peirano | 128/173.2 |
| 2,857,801 | 10/1958 | Murray | 88/14 |
| 3,040,742 | 6/1962 | Eichelman | 128/200.18 |
| 3,075,523 | 1/1963 | Eichelman | 128/200.18 |
| 3,077,307 | 2/1963 | Moore et al. | 239/338 |
| 3,353,536 | 11/1967 | Bird et al. | 128/194 |
| 3,527,411 | 9/1970 | Colgan | 239/338 |
| 3,652,015 | 3/1972 | Beall | 128/200.21 |
| 3,724,454 | 4/1973 | Brown | 128/194 |
| 3,744,771 | 7/1973 | Deaton | 261/78 |
| 3,836,079 | 9/1974 | Huston | 239/74 |
| 3,874,379 | 4/1975 | Enfield et al. | 128/194 |
| 3,898,429 | 8/1975 | Chodak | 219/307 |
| 3,913,843 | 10/1975 | Cambio, Jr. | 239/338 |
| 4,007,238 | 2/1977 | Glenn | 261/78 |
| 4,101,611 | 7/1978 | Williams | 261/142 |
| 4,116,387 | 9/1978 | Kremer, Jr. et al. | 239/338 |
| 4,177,945 | 12/1979 | Schwartz et al. | 239/338 |
| 4,201,204 | 5/1980 | Rinne et al. | 128/203 |
| 4,243,396 | 1/1981 | Cronenberg | 55/238 |
| 4,267,974 | 5/1981 | Kienholz et al. | 239/74 |
| 4,268,460 | 5/1981 | Boiarski et al. | 128/200.16 |
| 4,299,355 | 11/1981 | Hakkinen | 239/338 |
| 4,333,450 | 6/1982 | Lester | 128/200.18 |
| 4,427,004 | 1/1984 | Miller | 128/200 |
| 4,635,857 | 1/1987 | Hughes | 128/200.18 |
| 4,702,415 | 10/1987 | Hughes | 128/200.18 |
| 4,706,663 | 11/1987 | Makiej | 128/200.18 |
| 4,767,576 | 8/1988 | Bagwell | 128/200.18 |
| 5,152,456 | 10/1992 | Ross et al. | 128/200.16 |
| 5,259,370 | 11/1993 | Howe | 128/200.14 |
| 5,261,601 | 11/1993 | Ross et al. | 128/200.16 |

FOREIGN PATENT DOCUMENTS 22401 of 1906 United Kingdom .

*Primary Examiner*—Kimberly L. Asher
*Attorney, Agent, or Firm*—Poms, Smith, Lande & Rose

[57] ABSTRACT

A high flow rate humidifier employs a mixing body having a high pressure oxygen (128) jet that entrains water from a container (121) to provide a turbulent aerosol mixture of gas having water particles entrained therein. To remove the water particles and introduce vapor into the mixture, the mixture is passed through an evaporation chamber (200) formed by a pair of juxtaposed mutually spaced discs (202,204), each of which has a number of square holes (212a, 212b, 222a, 222b). The turbulent aerosol mixture at and about the jet orifice (132) is caused to flow linearly through the holes of the first disc into the space between the two, where it again becomes turbulent. The turbulent flow from between the discs is caused to flow linearly through the holes in the second or output disc into a mixing chamber (146) from whence the humidified gas is discharged.

5 Claims, 2 Drawing Sheets

HIGH FLOW RATE HUMIDIFIER WITH BAFFLE PLATES

This is a continuation of application Ser. No. 07/794,733, filed on Nov. 15, 1991, for High Flow Rate Humidifier, now abandoned.

The present invention is related to an application of Blair Howe for Nebulizer Heater, Ser. No. 422,310, filed Oct. 16, 1989, which issued as U.S. Pat. No. 5,063,921 on Nov. 12, 1991.

BACKGROUND OF THE INVENTION

Moisturized and oxygen enriched air is frequently used for inhalation therapy in a variety of different patient conditions. Different types of instruments, nebulizers for providing water particles, and humidifiers for providing water vapor, are used for different inhalation therapies. Some of these therapies require use of a nebulizer to provide moisturized oxygen enriched air in which the moisture is in the form of particles. The nebulizer provides moisture that is forced deep into the patient's lungs. However, a humidifier rather than a nebulizer is employed where it is desired to moisten tissues within the breathing passages of the patient, and where injection of water particles more deeply into the patient's breathing passages and lungs is not desired.

Nebulizers of various types can provide a wide range of total flow rates of moisturized breathing mixture to the patient from very small amounts, in the order of 10 liters per minute or less, to high amounts, as high as 100 liters per minute or more. However, most bubble type devices, a simple type in which a stream of air or oxygen enriched air is caused to flow or bubble through a liquid to entrain water vapor, are capable of total output flow rates of no more than about 10 to 12 liters per minute. If a higher flow rate of humidified breathing gas mixture is required, exceedingly complex and very costly ventilating equipment must be employed to provide the desired high flow rate of vapor entraining air mixtures. These systems use complex arrangements of flow generators, ventilators and heated humidifying equipment. Such arrangements may cost in the order of many tens of thousands of dollars, as compared to disposable nebulizers or humidifiers which may be available for as little as $10.00 or less. Inexpensive disposable humidifiers of high flow rates are not available.

In a treatment known as Constant Positive Airway Pressure (CPAP), a continuous positive pressure of moisturized breathing mixture is provided to the patient. Such treatment at present is performed with the exceedingly expensive ventilating equipment, which is effective over long periods. Alternatively, such treatment can be performed with a disposable gas injection nebulizer, such as shown in U.S. Pat. No. 4,767,576 for Nebulizer with Auxiliary Gas Input, assigned to the assignee of the present application. Such a nebulizer is effective for use in the CPAP treatment for relatively short periods of time, but must be turned off periodically in order to avoid excessive water build-up in the patient's breathing mask.

Accordingly, it is an object of the present invention to provide a moistened breathing mixture that contains water vapor but minimal water particles and which can provide a very high flow rate of the vapor entraining breathing mixture at relatively low cost.

SUMMARY OF THE INVENTION

In carrying out principles of the present invention in accordance with a preferred embodiment thereof a pressurized gas is moistened by aspirating water into it to provide an aerosol mixture of gas and water particles. The mixture is then passed through an evaporation chamber in which water particles are removed and further evaporation takes place to humidify the mixture by adding additional water vapor to the gas. This humidifying of the mixture is achieved by an apparatus comprising a mixing body in which a gas jet is caused to project a stream of gas that entrains liquid aspirated from a liquid container to provide a pressurized turbulent flowing aerosol mixture of gas and water particles. The pressurized mixture is transmitted to an aerosol mixing chamber through an evaporation device which coalesces water particles and causes them to drop from the aerosol mixture, while at the same time vaporizing some of the water particles to add further water vapor to the gas. According to a feature of the invention, the evaporation chamber is formed by a pair of juxtaposed mutually spaced perforated discs through which the aerosol mixture of gas and water particles is passed, causing the water particles to coalesce into larger droplets, which are collected for further use, and also causing vaporization of some of the water particles to further vaporize the gas.

DESCRIPTION OF THE PREFERRED EMBODIMENTS

Figure 1:
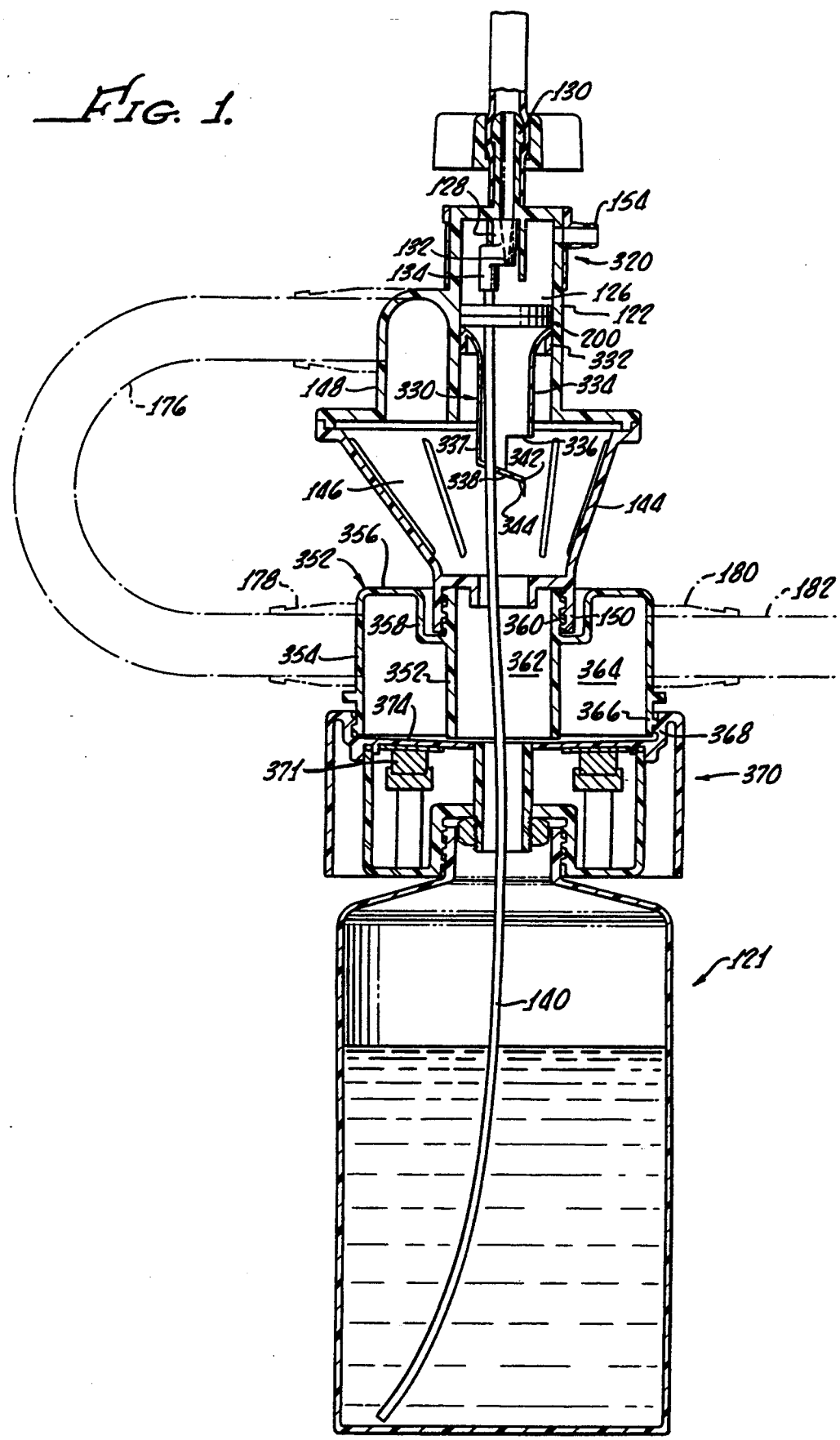
FIG. 1 is a cross sectional view of a humidifier embodying principles of the present invention.

FIG. 1 illustrates a nebulizer and heater of the configuration shown in FIG. 10 of the above identified related U.S. Pat. No. 5,063,921, but modified by an auxiliary air injection fitting and addition of an evaporation chamber embodying principles of the present invention. A nebulizer head or mixer body 320 includes a downwardly tapered aerosol mixing chamber housing section 144 and an upper air entrainment section 122 which respectively define an aerosol mixing chamber 146 and an air entrainment chamber 126. Mounted within the chamber 126 is a jet fitting 128 connected to an input oxygen fitting 130 and having a nozzle 132 positioned adjacent a suction fitting 134 that is connected to a suction tube 140. An auxiliary gas or air injection fitting 154 is provided in the upper air entrainment section 122 for connection to a pressurized air source so as to provide auxiliary pressurized air into the entrainment chamber 126. A venturi tube 330 is provided to increase flow velocity of aerosol into the mixing chamber 146 and provides improved precipitated droplet collection. The venturi tube 330 is fixedly positioned within the neck 332 of the mixer body below the fitting 128 and has a lowermost portion of its shank 334 cut away to form a large opening, as at 336. One side 337 of the shank extends downwardly to the end of the venturi tube 330 and has fixed thereto a downwardly inclined bottom plate 338, having a downwardly projecting wedge shaped and pointed drip member 344 secured to its lowermost free edge 342. Suction tube 140 extends through an aperture in bottom plate 338 of the venturi tube, through an accumulator housing 352 and a heater chamber 370 to a container 121. The accumulator housing 352 includes an outer circular wall 354 and a circular inner wall 351 concentric therewith and integrally connected with the outer wall by an upper wall 356. The latter has an inner stepped vertical portion 358 that is spaced radially outwardly of an upper end portion 360 of the tubular inner wall 351. Tubular wall 351 and 360 defines an inner or precipitate chamber 362 and cooperates with outer wall 354 to define an annular outer accumulator flow passage 364. The upper portion of the tubular wall is externally threaded to receive an internally threaded connecting nipple 150 of the mixing chamber section 144. The accumulator chamber housing has a lower end portion 366 that is externally threaded to receive internal threads on an upper portion 368 of a heater housing 370.

The heater housing includes a heater 371 that heats a flat heater platen 374 that is spaced just below the lower edge of the inner tubular wall 352 of the precipitate chamber. Mixing chamber 146 discharges its mixture through a discharge fitting 148, thence through a hose 176 connected to an input fitting 178 of the accumulator chamber 364. An output fitting 180 of accumulator chamber 364 is connected to an output hose, such as hose 182, that forms part of a conduit system connected to the patient's breathing apparatus.

The apparatus described to this point forms a heated nebulizer which is nearly the same as the nebulizer illustrated in FIGS. 10 and 11 of the above identified U.S. Pat. 5,063,931, differing primarily by the addition of the input pressurized auxiliary air fitting 154 which replaces the apertures used for aspirating air into the upper portion of the mixer body in the arrangement of the prior application. The evaporation chamber embodying principles of the present invention has not yet been described.

A detailed description of this nebulizer apparatus may be found in the above-identified U.S. Pat. No. 5,063,921. Briefly, the apparatus operates as follows, without the evaporation chamber. Oxygen under pressure is fed via fitting 130 to the jet nozzle 132 and thereby aspirates water from container 121, through suction tube 140 and aspirating fitting 134 to be mixed in the upper portion of the mixer body, designated as entrainment chamber 126, with the oxygen from fitting 130 and the pressurized air introduced via fitting 154 (the related U.S. Pat. No. 5,063,921 uses aspirated rather than pressurized air). The combination of pressurized air and pressurized oxygen input entrains the aspirated water and creates a turbulent flow of aerosol within the upper portion of the mixer body, that is within air entrainment chamber 126.

The turbulent pressurized flow of aerosol mixture of gas and entrained water particles is projected downwardly against plate 338, which helps to collect water droplets which are precipitated out of the entrainment chamber 126 to drop through mixing chamber 146 and chamber 362 onto the heater platen 374. The aerosol mixture flows in a turbulent swirling pattern within chamber 146 and then out through fitting 148 and connecting conduit 176 into the circular passage of accumulator chamber 364, from which it is discharged via fitting 180 and tube 182. Pressure within the precipitate chamber 362 forces accumulated water at the bottom of this chamber to flow beneath the lower end of circular inner wall 351 radially outwardly along the heater platen 374 where it is heated and vaporized so as to generate water vapor that is added to the mixture within chamber 364 for discharge to the patient. Total output flow rate of this apparatus can be as high as 100 liters per minute.

Although baffling is provided in the mixing chamber 146, and the venturi tube tends to help collect water particles, the aerosol mixture, without the evaporation device 200, to be described below, still contains a large quantity of water particles in addition to a relatively small amount of water vapor. Thus the device so far described, omitting the evaporation device 200, operates as a nebulizer that is capable of providing high total output flow rates, a moisturized breathing mixture of air, oxygen and water particles. However, as previously mentioned, it is desirable in many instances to provide such a breathing mixture at a desired high total output flow rate, in the order of between 20 and 100 liters per minute total output flow, which is substantially free of water particles but which does entrain a significant amount of water vapor.

To remove at least a major portion of the water particles from the discharged aerosol mixture, and to increase the amount of entrained water vapor, applicant provides the evaporation device 200 fixedly mounted on the upper flared end of venturi tube 330 in entrainment chamber 126. The device 200 extends completely across the venturi tube, so that all fluid passing from chamber 126 to chamber 146 must pass through the evaporation device.

Figure 2:
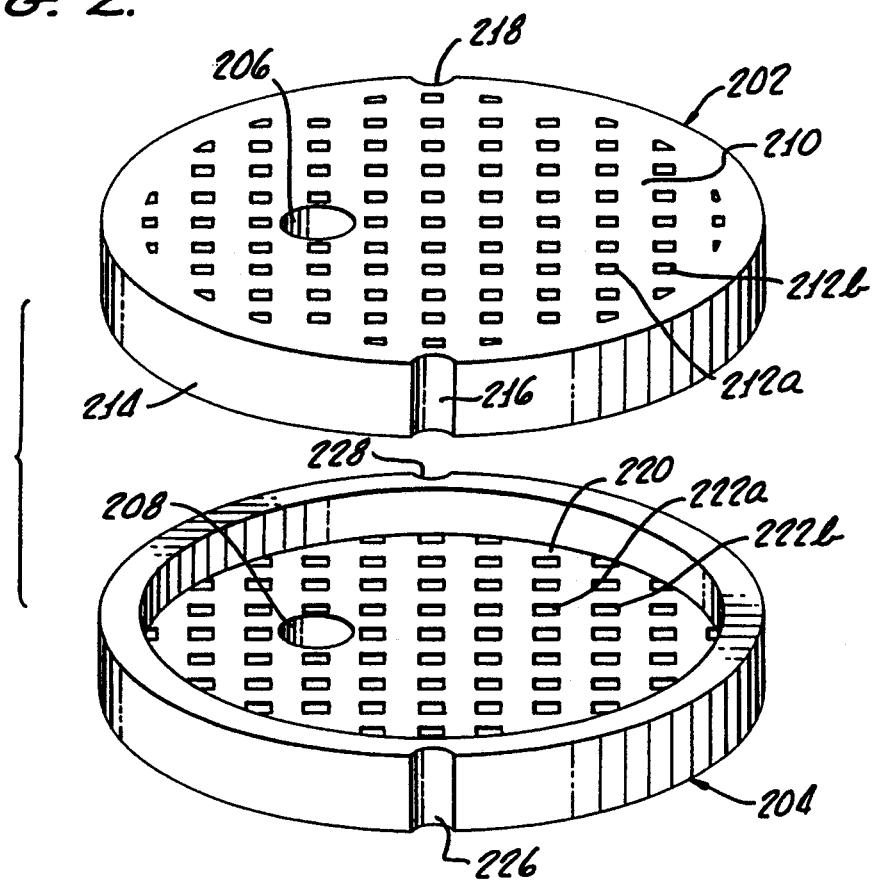
FIG. 2 is a pictorial exploded view of the evaporation chamber formed by the two perforated discs.
Figure 3:
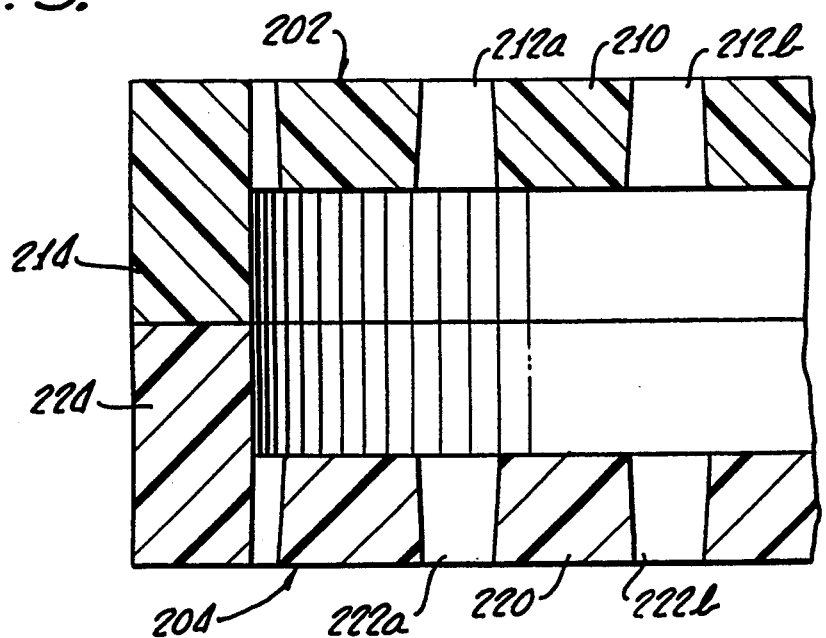
FIG. 3 is an enlarged cross sectional view of a pair of juxtaposed spaced evaporation chamber discs.

Evaporation device 200 (see FIGS. 2 and 3) comprises upper and lower or input and output discs 202 and 204, which are identical to each other, except for the opposite hand locations of hole 206 in disc 202 and hole 208 in disc 204, which receive the suction tube 140. Except for this difference in orientation of the suction tube receiving hole, the discs may be identical. Each disc comprises a circular disc plate 210 having a large number of apertures, generally indicated at 212a and 212b, which extend through the disc plate 210. Formed integrally with the plate 210 is a continuous upstanding peripheral skirt 214 that projects from one side of the plate 210 in a direction perpendicular to the plane of the plate. A pair of oppositely disposed orientation notches 216 and 218 are provided on the discs for cooperation with small keys (not shown) on the interior of walls of mixing body portion 122 to fix the orientation of the evaporation device to receive the off axis tube 140.

The output disc 204, as mentioned, is identical, except for the location of the hole 208, to the input disc 202, having a main plate 220 with holes 222a and 222b extending through the plate. The hole pattern of disc 204 is aligned with the hole pattern of disc 202 so that each hole in one disc is aligned with a hole in the other disc. A projecting peripheral continuous skirt 224 is secured to the plate 220, and orientation notches 226,228 are provided, aligned with the corresponding orientation notches 216,218 of disc 202. The two discs are juxtaposed with the free edges of their skirts 214,224 in contact with one another so that the disc plates 210 and 220 are spaced from one another by twice the depth of either one of the skirts.

In a particular exemplary embodiment each disc has a diameter of about 1.10 inches, having a total thickness of plate and skirt of about 0.1 inch. Each skirt and plate individually has a depth of 0.05 inches, to provide the total disc thickness of 0.1 inches. In this embodiment each disc has a total of 67 holes positioned in a regular rectangular array, approximately 0.1 inches on centers. It will be understood that other numbers of holes and other array patterns can be employed as deemed necessary or desirable. Each hole at its outer side has a square configuration of about 0.03 inches on each side. Each hole has a slight taper of approximately 1°, being wider at its inner side than its outer side. Preferably, the discs are molded of a suitable heat resistant polymer, such as impact modified styrene or a modified propylene. A pair of discs is assembled in the arrangement illustrated in FIGS. 1 and 3 and fixedly positioned within the mixer body on the upper end of the venturi tube 330.

The apparatus with the evaporation device installed operates in a manner similar to that previously described, except for the important fact that the evaporation device 200 effectively removes significant quantities of water particles entrained in the aerosol mixture and concomitantly vaporizes much of the water so as to add larger quantities of water vapor to the mixture. In operation of the apparatus with the evaporation device in place, the input pressurized oxygen from fitting 130 and pressurized air from fitting 154 effectively aspirate water to provide a pressurized turbulent flow within entrainment chamber 126 of a moisturized mixture of gas (oxygen enriched air) and water particles. Pressure in chamber 126 forces this mixture to pass through the evaporation device into the mixing chamber 146. In traversing the evaporation device, water particles are removed from the gas and increased evaporation takes place to add vapor to the gas. As the turbulent pressurized aerosol mixture within entrainment chamber 126 impinges upon the upper surface of evaporation chamber input disc 202, the water wets all surfaces of the disc. The aerosol mixture passes through the evaporation chamber. Water particles are forced through the holes 212a, 212b etc. of the upper disc, and because of the pressure of the gas flowing through the evaporation device, the water forms a very thin film along all disc surfaces, along the upper surface of plate 210, along the walls of each of the square apertures, and along the lower surface of plate 210, including the inner wall of skirt 214. Thus, a very large area of water (and concomitantly a smaller volume, because of the thin film of water) is provided in contact with the gas, thereby greatly enhancing evaporation of the water. The resulting vapor is picked up by the flowing gas.

Space 230 between the input and output perforated discs 202,204 effectively comprises an evaporation chamber. Turbulent gas flow to the evaporation device passes through the apertures 212a, 212b etc. and is effectively linearized by the apertures. The linearized flow disperses outwardly, at least partly because of the taper of the apertures, to create once more a turbulent flow within the chamber 230. The moisturized gas is caused to pass through the second of the evaporation plates, passing in a linear flow through the apertures 220a, 220b etc. of the lower plate 220 to flow into the mixing chamber 146. Again, water droplets wet all surfaces of the lower plate, forming a thin film of water on all of its internal surfaces and upon its lower surface, including the inner surfaces of the apertures, thereby providing further increase of area of the thin water film, to thereby increase vaporization. Even though hole patterns are aligned in the two discs, so that holes in one plate are axially aligned with holes in the other, straight flow through both discs is prevented by thin film wetting of hole surfaces and turbulence in the chamber between the discs. Portions of the thin film of water that wets the wall surface of the holes and are not vaporized tend to coalesce into larger water droplets as the water leaves the holes, and such droplets are effectively precipitated from the mixture since they are too large to be entrained in the flowing gas stream. Moreover, the establishment of the thin film of water provides for a relatively long residence time of the water on or within the surfaces and chamber of the evaporation device, and thus increases the time during which the thin film of water may vaporize to be taken up as water vapor by the gas flowing through the evaporation chamber 230.

Evidence of efficiency of the evaporation is provided by the unexpectedly large decrease in temperature of the aerosol as it flows from the evaporization chamber. Tests have show temperature of aerosol after passing through the evaporation chamber to be 15° F. lower than the temperature of aerosol in the same part of the same apparatus with the evaporation device omitted.

Although square, rectangular or other non-circular holes in the evaporization discs are preferred because of the increased wall surface area provided by such a rectangular configuration, holes of circular configuration will operate, but with a decreased amount of vapor production and decreased amount of vapor induced into the gas.

Some degree of water particle removal and increased vaporization may be provided by use of a porous membrane in the place of the vaporization discs described. For example, a membrane made of an open celled porous polyethylene material known under the trademark POREX made by Porex Technologies, may be employed in the place of the discs 202 and 204. However, such a porous membrane is not nearly as effective as the perforated discs which provide a surprisingly and unexpectedly great improvement in both vapor entrainment and particle removal as compared to the open celled plastic membrane. The two discs provide flat surfaces for collection of the water, which is thus more effectively removed from the turbulent aerosol mixture. The water wets substantially all of the large surface area of the perforated discs and is forced through the apertures by the pressurized aerosol flowing through the air entrainment chamber.

The square holes are more efficient than round holes, because, in part, with the round holes, water particles tend to ball up and drop through the holes, whereas, with the square or rectangular holes, water tends to cling to the hole surface, wetting both sides of the plates and sides of the hole.

Although the described apparatus may be useful in the configuration described, wherein it is combined with the accumulator chamber 352 and heater chamber 370, principles of the present invention may be used in many other configurations. Thus the apparatus may be used as a high flow rate humidifier in a basic air entrainment nebulizer configuration, without the input of pressurized gas through auxiliary nozzle 154. Such a nebulizer without the auxiliary pressurized air input is shown in U.S. Pat. No. 4,629,590 for Nebulizer, invented by James T. Bagwell, and U.S. Pat. No. 4,819,625 for Nebulizer Heater, invented by Blair E. Howe, both assigned to the assignee of the present invention. Further, the accumulator chamber 352 and heater 370 may be removed from the assembly, with the mixing chamber 144 connected directly to the water container 122. In such a case discharge from the apparatus of a breathing mixture is provided from the discharge fitting 148 to the patient's breathing apparatus. Many other configurations will be readily apparent. Nevertheless, in each configuration there is provided an inexpensive humidifier providing a total output flow rate of up to 100 liters per minute in which a breathing mixture is provided having a maximum of entrained water vapor and a minimum of entrained water particles.

The foregoing detailed description is to be clearly understood as given by way of illustration and example only, the spirit and scope of this invention being limited solely by the appended claims.

What is claimed is:

1. A high flow rate humidifier comprising:

a mixer housing having a mixing chamber therein, jet nozzle means in said housing for receiving a pressurized gas and projecting a stream of high velocity gas towards said mixing chamber, means adjacent said jet nozzle means for aspirating a liquid into said mixer housing adjacent said jet nozzle means, thereby entraining liquid in said projected stream, evaporation enhancing means interposed between said nozzle means and said mixing chamber in the path of the stream projected from said nozzle means for passing said high velocity projected stream to said mixing chamber and causing coalescence of liquid entrained in said jet stream into coalesced particles that are transported into said mixing chamber and for increasing evaporation of water to provide humidified gas in said mixing chamber, said evaporation enhancing means comprising an evaporation chamber defined at least in part by first and second closely spaced plates each having a plurality of perforations, said first plate comprising:

a first perforated disc, a first integral continuous upstanding skirt projecting from a first side of said first disc in a direction perpendicular to the plane of said disc and having a free edge, said second plate comprising:

a second perforated disc, a second integral continuous upstanding skirt projecting from a first side of said second disc and having a free edge, said first and second discs being juxtaposed with said first side of said first disc facing said first side of said second disc and with said free edges of said first and second skirts in contact with one another so that said first and second discs are mutually spaced by the combined depth of said first and second skirts, said first and second discs and said contacting skirts collectively defining said evaporation chamber, and means for discharging humidified gas from said mixing chamber.

2. The humidifier of claim 1 wherein said perforations each has a dimension of about 0.03 inches.

3. The humidifier of claim 2 wherein said plates are mutually spaced by about 0.1 inches, and wherein each of at least a group of said perforations is rectangular and perforations of both said plates are wider at inner sides of said plates than at outer sides of said plates.

4. The humidifier of claim 1 wherein said first and second perforated discs have mutually aligned aspiration tube holes, and wherein said means for aspirating a liquid comprises a tube extending through said mixing chamber and through said aspiration tube hole, each said skirt having an orientation element for fixing orientation of discs relative to one another and relative to said mixing chamber.

5. A high flow rate humidifier comprising:

a mixer housing having a liquid entrainment chamber and an aerosol mixing chamber connected thereto, jet means in said liquid entrainment chamber for projecting a stream of gas said entrainment chamber into said mixing chamber, means said entrainment chamber for drawing a liquid into said entrainment chamber and mixing such liquid with said stream of projected gas within said entrainment chamber to provide an aerosol in said entrainment chamber that is projected toward and into said mixing chamber, evaporation means including first and second plates interposed between said entrainment and mixing chambers for receiving the gas stream projected from said jet means and coalescing particles of liquid therefrom, and for evaporating liquid from said stream, said first and second plates including means for passing the stream projected from said jet means together with liquid entrained therein from said entrainment chamber to said mixing chamber, said first plate comprising:

a perforated disc, a first integral continuous upstanding skirt projecting from a first side of said first disc in a direction perpendicular to the plane of said disc and having a free edge, said second plate comprising:

a second perforated disc, a second integral continuous upstanding skirt projecting from a first side of said second disc and having a free edge, said first and second discs being mutually juxtaposed with said first side of said first disc facing said first side of said second disc and with said free edges of said first and second skirts in contact with one another so that said first and second discs are mutually spaced by the combined depth of said first and second skirts, said first and second discs and said contacting skirts collectively defining said evaporation chamber, and means for discharging humidified gas from said mixing chamber.

* * * * *